United States Patent [19]
Fitzgerald

[11] 4,361,151
[45] Nov. 30, 1982

[54] TAMPON

[75] Inventor: Harry G. Fitzgerald, Green Bay, Wis.

[73] Assignee: Tech-Tran, Inc., Green Bay, Wis.

[21] Appl. No.: 213,256

[22] Filed: Dec. 5, 1980

[51] Int. Cl.³ .............................................. A61F 13/20
[52] U.S. Cl. .................................................. 128/285
[58] Field of Search ....................... 128/263, 270, 285

[56] References Cited
U.S. PATENT DOCUMENTS

| | | | |
|---|---|---|---|
| 2,386,590 | 10/1945 | Calhoun | 128/285 |
| 2,509,241 | 5/1950 | Mende | 128/263 |
| 3,138,159 | 6/1964 | Schmidt | 128/285 |
| 3,397,695 | 8/1968 | Voss | 128/285 |
| 3,409,011 | 11/1968 | Mittag | 128/285 |
| 4,212,301 | 7/1980 | Johnson | 128/285 |

*Primary Examiner*—C. Fred Rosenbaum
*Attorney, Agent, or Firm*—Wheeler, House, Fuller & Hohenfeldt

[57] ABSTRACT

A tampon formed from braided slivers of absorbent material, having a head portion which is less compressed axially and radially than a tail portion thereof. The braided body can be folded in half to define a tampon with a folded head portion and a bifurcated tail portion. Such tampons are adapted for insertion with the head portion foremost into a body cavity.

Furthermore, a tampon applicator tube comprising a cylindrical handle and a flared insertion end which engages a shoulder behind the enlarged head of the tampon to allow the tampon to be inserted in place. The applicator tube is not necessarily provided with a plunger to aid insertion.

16 Claims, 7 Drawing Figures

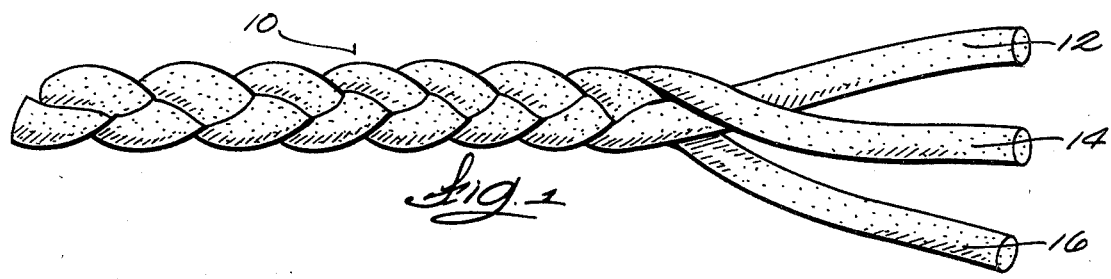
fig. 1
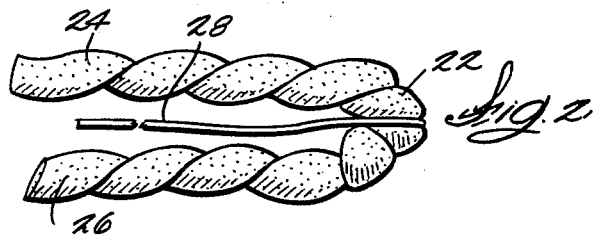
fig. 2
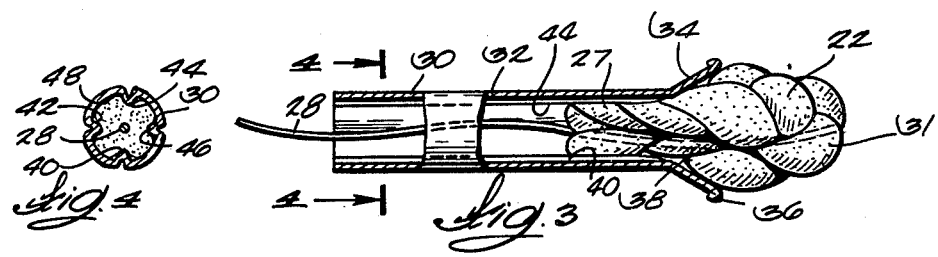
fig. 4
fig. 3
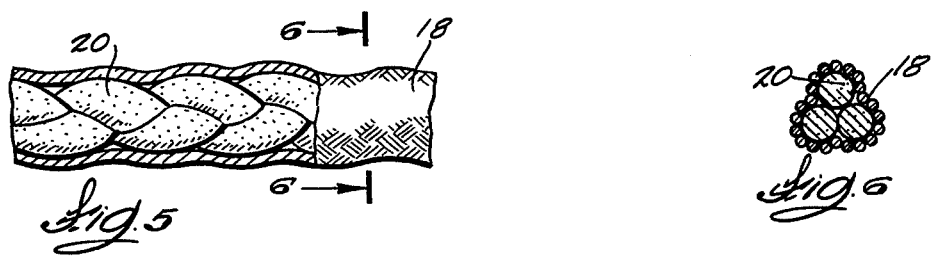
fig. 5
fig. 6
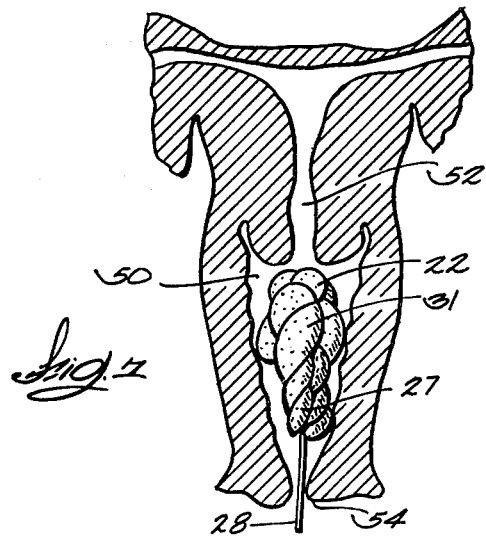
fig. 7

TAMPON

BACKGROUND OF THE INVENTION

This invention relates to a tampon for insertion into a body cavity to absorb and contain a largely fluid discharge. This invention especially relates to tampons used to contain menstrual flow.

Tampons are well known devices to absorb the flow of body excreta, particularly menstrual fluids. The desired features of a tampon are a large initial and total capacity for fluids, easy and comfortable insertion and withdrawal, and means to warn of the need to replace the tampon. These requirements for a tampon are widely known and sought after, but are not easily met.

Prior tampons have several disadvantages. They do not provide any signal to indicate the need to replace the tampon just before it is saturated. The lack of such a signal worries the user and encourages her to replace the tampon long before saturation is approached. In prior tampons the absorbent material has not been concentrated at the end of the tampon which is inserted furthest into the vagina. In fact, the art teaches that folded tampons should be positioned in the vagina with the folded portion furthest from the uterus, so that the absorbent material is not concentrated at the source of menstrual fluid.

Prior tampons also are not built to provide a high total absorbency and wicking rate while avoiding any tendency to slough material from the tampon upon withdrawal. A tampon constructed of loose or unconfined fibers or strands can lose fibers and the fibers can become disarranged and spread out during insertion or wear of the tampon. Thus, a tampon made of loose or unconfined fibers has a poor wicking rate because the capillary spaces are too large. If the tampon is tightly bound together to prevent sloughing, for example by sheathing it in a woven mesh, the fibers can become too confined, collapsing the capillary spaces between the fibers and thus reducing total absorbency. In an optimized absorbent structure, the needs to promote wicking and absorbency and prevent sloughing are balanced to form a moderately compressed structure which does not tend to slough off fibers or other structures.

SUMMARY OF THE INVENTION

The invention is an absorbent tampon comprising plural slivers of absorbent material braided together to form an absorbent braided body. The tampon can comprise a single length of braided material, but preferably comprises a double length of braided material folded in half to form a folded head portion and a trailing bifurcated tail portion. The head portion of the tampon is radially larger and less dense than the tail portion; the tail portion is more highly compressed both axially and radially than the head portion. As a result of this compression profile, the head portion of the tampon, which is positioned in the vagina nearest the uterus during use, contacts menstrual fluid first and rapidly absorbs it and expands to prevent the bypass of fluid.

When the tampon is near saturation its tail portion, which absorbs and wicks fluid more slowly than its head portion, expands axially. The head portion of the tampon is anchored in place by its relatively large expansion. Thus the tail portion expands axially and gently presses against the nerve endings near the mouth of the vagina to signal that saturation of the tampon is imminent.

Another part of the present invention is an improved insertion tube for the foregoing tampon. The insertion tube has a flared insertion end which engages the shoulder formed at the base of the protruding enlarged head of the tampon and thus bears against the head of the tampon during insertion. The insertion tube can be made in one piece or can include a plunger to aid insertion.

BRIEF DESCRIPTION OF DRAWINGS

FIG. 1 is a side elevation of an absorbent body comprising braided slivers of absorbent material.

FIG. 2 is a side elevation of a folded braided absorbent body, including a withdrawal string.

FIG. 3 is a side view, partly in cross-section, of an assembled tampon and applicator tube before insertion of the tampon into a body cavity.

FIG. 4 is a cross-section of FIG. 3 taken along line 4—4.

FIG. 5 is a fragmentary side elevation of an alternate embodiment of the structure of FIG. 1, partially cut away to show a braided core enveloped in a braided cover.

FIG. 6 is a cross-section of the embodiment of FIG. 5 taken along line 6—6 thereof.

FIG. 7 is a longitudinal cross-section of the lower reproductive tract of a female mammal, showing the present invention in place to control menstrual flow.

DESCRIPTION OF THE PREFERRED EMBODIMENTS

Although the disclosure hereof is detailed and exact to enable those skilled in the art to practice the invention, the physical embodiments herein disclosed merely exemplify the invention which may be embodied in other specific structure. While the best known embodiment has been described, the details may be changed without departing from the invention, which is defined by the claims.

In the drawings, FIG. 1 shows an absorbent body 10 comprising three slivers 12, 14 and 16 of absorbent material braided together. As in the prior art, each sliver is an axially elongated batt of carded fibers which are substantially parallel to each other. Braiding is broadly defined herein to include any method of interweaving slivers together to form an elongated structure which cannot unravel from the middle. While in this embodiment of the invention three slivers are braided together, it will be understood that any number of slivers, for example as few as three and as many as ten, can be braided together as described herein using well known techniques.

The braiding shown in FIG. 1 prevents the slivers from unraveling into their constituent fibers. As another result of braiding each sliver periodically plunges into the interior of the body, so fluids wicking along a sliver in the fiber direction are conducted from the outside of the body to its interior. The braiding shown in FIG. 1 also creates a network of larger capillary spaces between adjacent slivers which also encourage wicking of fluids from the outside of the structure to the inside thereof. But braiding does not so tightly constrict the slivers as to collapse the capillary spaces between their adjacent fibers.

An alternate absorbent structure is shown in FIGS. 5 and 6. In this embodiment a braided sheath 18 encloses an absorbent core 20. The sheaths, the absorbent core or both may be formed from braided slivers of absorbent material. The sheath prevents sloughing of the core, which can include particles of highly absorbent non-fibrous materials such as copolymers of acrylonitrile and starch. But sheath 18 has radial and axial give, unlike gauze or netlike or woven materials, so the enveloped core can readily expand to accommodate absorbed fluids.

The absorbent braided body 10 in FIG. 1 can be used directly as a tampon element, providing that its diameter is appropriate to allow insertion and to provide maximum absorbency. Such absorbent bodies have a diameter of from 0.5 inches to 1.5 inches in the uncompressed state, and a diameter under compression of from 0.5 inches to 0.7 inches.

Alternatively, the braided structure 10 in FIG. 1 can be folded in half as shown in FIG. 2 to form a folded head portion 22 and trailing ends 24 and 26 which define a bifurcated tail portion 27 (best shown in FIG. 3). In the embodiment of FIG. 2, the presence of a fold adjacent head portion 22 concentrates absorbent material at the head of the tampon. A withdrawal string 28 may be tied to the head portion 22 of the structure shown in FIG. 2; string 28 is draped between trailing ends 24 and 26 and extends therebeyond a substantial distance to provide for withdrawal of the tampon at a suitable time.

FIG. 3 shows the tampon of FIG. 2 suitably compressed and inserted into an improved applicator tube. Comparing the tampon of FIG. 3 to that of FIG. 2, the head portion 22 in FIG. 3 has been only slightly compressed radially and axially, and the tail portion 27 has been highly compressed both axially and radially. As a result, head portion 22 is radially larger and less tightly packed in FIG. 2 than the tail portion 27. This differential compression of head portion 22 and tail 27 of the tampon allows the head portion 22, which is positioned nearest the uterus in use, to have a greater absorbent capacity per gram of material and to wick material into its interior faster than the material of tail portion 27. When the tampon is in place, head portion 22 rapidly absorbs incoming fluid and easily deforms laterally outward in the vagina to prevent the fluid from bypassing the tampon. Tail portion 27 of the tampon does not receive fluid initially because it is positioned away from the site of discharge and it is tightly packed to reduce its wicking rate. But when head portion 22 becomes nearly saturated, liquid begins to wick into tail portion 27, causing it to expand axially. Since head portion 22 anchors the tampon in place while it is in use, tail portion 27 expands axially downward in the vagina. This axial expansion brings the tail portion 27 of the tampon into contact with the sensitive region of the vagina near its mouth and thus signals to the user that a replacement tampon is needed soon.

FIG. 3 also shows an assembly of an applicator tube 30 and a tampon 31. Applicator tube 30 comprises a hollow tube, preferably made of plastic or cardboard, and preferably biodegradable. Tube 30 has a handle portion 32 which is generally cylindrical and a flared insertion end 34 which preferably has an outwardly rolled edge 36 to strengthen the insertion end and to prevent discomfort during insertion. Because head portion 22 of tampon 31 is larger than its tail portion 27, the intersection of the head and tail portions defines a shoulder 38 which seats against insertion end 34. Withdrawal string 28 extends through handle portion 32 and out the other side, in the usual fashion.

FIG. 4 shows the preferred construction of applicator tube 30. Handle portion 32 of applicator tube 30 has ribs 40, 42, 44 and 46 which extend radially inward from inside wall 48 to strengthen the applicator tube and to limit the surface area of tail portion 27 which frictionally engages the applicator tube before insertion.

The tampon and applicator tube assembly shown in FIG. 3 is used to insert tampon 31 within the upper part of vagina 50 as shown in FIG. 7. The tampon is inserted with its head portion 22 near the mouth of uterus 52, while the tail portion 27 of the tampon is located substantially within the vagina 50 nearest its mouth 54. Withdrawal string 28 extends through mouth 54 to provide for withdrawal of tampon 31.

The tampon is inserted by grasping handle portion 32 of the applicator tube 30, inserting the tube and tampon assembly into the vagina with head portion 30 foremost to position the tampon in the vagina, and then withdrawing applicator tube 38, leaving the tampon in place. In one embodiment of the invention, no plunger is needed within applicator tube 30 to maintain the position of the tampon during withdrawal of the applicator tube, for the head portion 22 of the tampon is sufficiently enlarged to prevent it from being dislodged by withdrawal of the applicator tube. However, it will be understood that the conventional telescoping applicator tube and plunger could be employed to aid insertion of the tampon. During insertion, flared insertion end 34 bears against shoulder 38 to propel head portion 32 of tampon 31 into the vagina without forcing the protruding end of the tampon into the insertion tube. The tampon is withdrawn in the usual manner.

I claim:

1. An absorbent tampon comprising plural slivers of absorbent material braided together to form an absorbent braided body.

2. The tampon of claim 1, wherein said body has a head portion and tail portion, said tail portion is highly compressed axially and radially, and said head portion is less compressed than said tail portion.

3. The tampon of claim 2, wherein said head portion has a greater diameter than said tail portion.

4. The tampon of claim 3, wherein at least a portion of said braided body comprises a sheath enclosing an absorbent core.

5. The tampon of claim 4, wherein said absorbent core comprises braided slivers of absorbent material.

6. The tampon of claim 4, wherein said core comprises a highly absorbent copolymer of starch and acrylonitrile.

7. The tampon of claim 1, wherein said absorbent braided body is folded in half to form a folded head portion and a bifurcated tail portion.

8. The tampon of claim 7, wherein said tail portion is highly compressed axially and radially, and said head portion is less compressed than said tail portion.

9. The tampon of claim 8, wherein said head portion has a greater diameter than said tail portion.

10. The tampon of claim 9, wherein at least a portion of said braided body comprises a sheath enclosing an absorbent core.

11. The tampon of claim 10, wherein said absorbent core comprises braided slivers of absorbent material.

12. The tampon of claim 10, wherein said core comprises a highly absorbent copolymer of starch and acrylonitrile.

13. The tampon of claim 1, further including a tampon applicator tube comprising a cylindrical handle portion and a flared insertion end.

14. The tampon and applicator tube of claim 13, wherein said tampon has a head portion and a radially smaller tail portion which intersect to form a shoulder, and wherein said tube has a cylindrical handle end and a flared insertion end to bear against said shoulder during insertion of said tampon head first into a body cavity.

15. The tampon and applicator tube of claim 14, wherein said tail portion is confined within said handle portion and at least a portion of said head portion protrudes forwardly from said flared insertion end.

16. The assembled tampon and applicator tube of claim 15, wherein said flared insertion end has an outwardly rolled forward edge.

* * * * *